United States Patent [19]
Sakakibara et al.

[11] Patent Number: 4,833,739

[45] Date of Patent: May 30, 1989

[54] STEAM SAUNA

[75] Inventors: Shigeru Sakakibara; Ryuici Kawamoto, both of Aichi, Japan

[73] Assignee: INAX Corporation, Tokoname, Japan

[21] Appl. No.: 169,644

[22] Filed: Mar. 17, 1988

[30] Foreign Application Priority Data

Mar. 26, 1987 [JP] Japan ................................. 62-73820

[51] Int. Cl.$^4$ ............................................. A61H 33/06
[52] U.S. Cl. ............................................. 4/524; 4/555
[58] Field of Search ................... 4/524, 555, 526, 527, 4/528, 529, 530, 531, 532, 533, 534; 68/3 SS, 5 D

[56] References Cited

U.S. PATENT DOCUMENTS

| 3,564,201 | 2/1971 | Jones et al. | 4/524 X |
| 3,668,905 | 6/1972 | Schlunke | 68/3 SS X |
| 4,398,308 | 8/1983 | Berg | 4/524 X |
| 4,565,188 | 1/1986 | Hardie | 4/524 X |
| 4,712,538 | 12/1987 | Hardie et al. | 4/524 X |

FOREIGN PATENT DOCUMENTS

| 2123739 | 12/1972 | Fed. Rep. of Germany | 4/524 |
| 3239049 | 5/1984 | Fed. Rep. of Germany | 4/524 |

Primary Examiner—Frankie L. Stinson
Attorney, Agent, or Firm—Frank J. Jordan; C. Bruce Hamburg; Manabu Kanesaka

[57] ABSTRACT

A steam sauna has a passage for circulation of air existing in a sauna booth, and is provided with a heater for heating air flowing through the passage, and a steam generator with an ultrasonic oscillator for mixing steam generated with the air heated.

8 Claims, 13 Drawing Sheets

STEAM SAUNA

FIELD OF THE INVENTION AND RELATED ART STATEMENT

This invention relates to a steam sauna for creating an atmosphere of comparatively low temperature and high humidity in a sauna booth.

Figure 3:
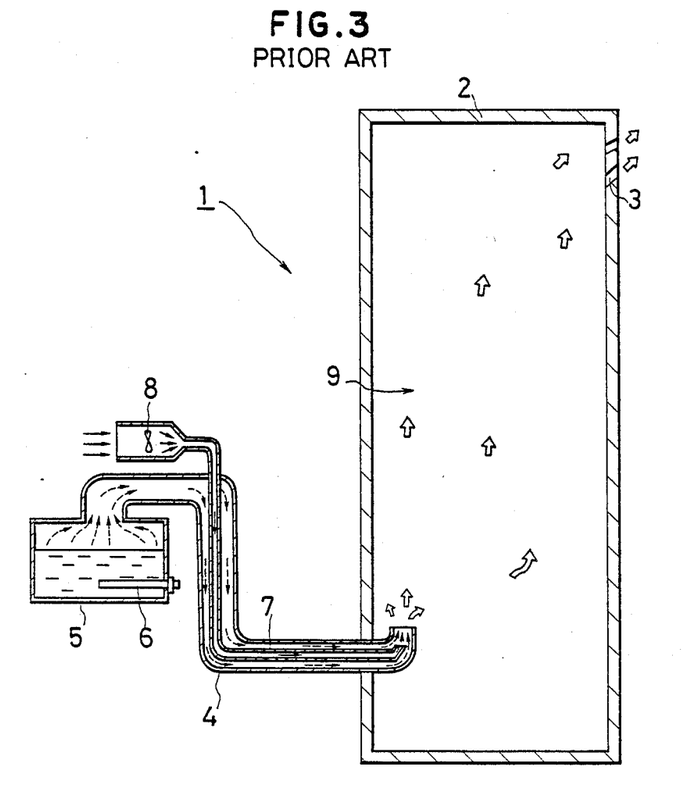
FIG. 3 is a vertical sectional view showing a sauna booth of a conventional steam sauna.
Figure 4:
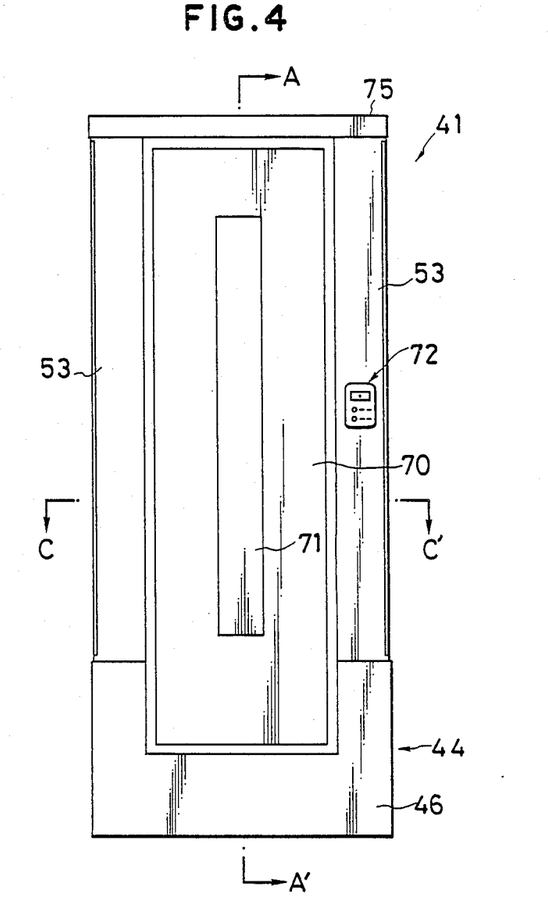
FIG. 4 is a front view showing a sauna booth according to a third embodiment of the present invention.

A conventional steam sauna of the above type is configured as shown in FIG. 3. That is, the conventional steam sauna 1 has discharge paths 3 formed in an upper section of a sauna booth 2 with a steam supply pipe 4 provided and opened in a lower section thereof. The steam supply pipe 4 supplies steam, generated by boiling reserved water stored in a water tank 5 by the use of a heater 6, into a room 9. On the other hand, an air supply pipe 7 provided inside the steam supply pipe 4 supplies fresh air by means of a fan 8, which spouts out the fresh air from its end located inside the steam supply pipe 4 and close to the output end thereof. Accordingly, the steam is mixed with the fresh air and spouted out into the room 9 of the sauna booth 2, so that the steam temperature is lowered, thereby creating an atmosphere of proper temperature and high humidity in the room 9. Incidentally, the reason for supplying the fresh air is that if only the steam generated by boiling the reserved water is spouted out into the room 9, the internal temperature of the room 9 becomes high enough to result in the danger of scalds. Mixed gas spouted out into the room 9 progressively rises inside the room and escapes out of the room through the discharge paths 3. During operation, the mixed gas is continuously spouted out into the room 9.

In the conventional steam sauna 1 described above, the steam generated through boiling and the fresh air are supplied after mixed and then discharged through the discharge paths 3; therefore, the heat energy of the mixed gas thus discharged is wasted and no efficient utilization of the heat energy can be attained. That is, the conventional steam sauna is defective in that the heat loss is large and the total amount of steam increases with time. In addition, since the steam is generated by boiling (heating to 100° C.) the reserved water stored in the water tank 5, the heater 6 must have a large capacity, normally of more than 3200 W, strong enough to boil the reserved water; this increasing the system size and raising the cost. The mixed gas of steam and fresh air forms streams flowing from the lower section to the upper section of the sauna booth 1, so that the mixed gas is not supplied thoroughly to all areas of the room 9; hence, variations appear in temperature and humidity throughout the inside of the room 9. Since the steam generated through boiling is mixed with the fresh air, the temperature of the mixed gas spouted out into the room 9 varies depending on an outside air temperature; this making it impossible to perform stable temperature control. Further, since at the beginning of spouting-out of the mixed gas the temperature of the wall surface of the sauna booth 2 stands equal to the outside air temperature, the heat energy of a part of steam coming into contact with the wall surface is taken away, thereby resulting in dew condensation.

Object and Summary of the Invention

The present invention has been devised to solve the foregoing problems.

It is a first object of the present invention to reduce the capacity of a heater for generating steam being introduced into a sauna booth.

It is a second object of the present invention to provide a steam sauna which exhibits little hear loss in a sauna booth, consumes a little power, and gives a good heat efficiency.

It is a third object of the present invention to provide a steam sauna which is capable of making uniform the internal temperature and humidity of a booth over all areas thereof.

It is a fourth object of the present invention to prevent dew condensation from appearing on the inside wall surface of a booth.

It is a fifth object of the present invention to make a steam sauna usable as a hot air sauna by supplying hot air alone.

It is a sixth object of the present invention to provide a steam sauna which makes a shower mode as well as a steam sauna mode enjoyable in the same booth.

Other objects will become apparent from the following description.

A steam sauna according to the present invention comprises a sauna booth, a passage for connecting one portion with another portion inside the sauna booth through which air existing in the sauna booth can circulate, a fan provided in the passage for circulating the air, a heater provided in the passage for heating the circulating air, and a steam generator with an ultrasonic oscillator for generating steam which is disposed so that the generated steam can be mixed with the air flowing through the passage.

In the steam sauna of the present invention, the heater or heat exchanger serving as heating means, disposed midway along the passage, previously warms the air existing in the sauna booth up to 40°–45° C. In this state, the ultrasonic oscillator is put into operation to vibrate reserved water stored in a water tank, so that a fog is generated in the passage. Hot air passing through the passage comes into contact with the fog to vaporize it, so that the resultant mixed fluid of steam and hot air is spouted out into the booth or room and circulates thereinside. The temperature of the circulating fluid including steam is 42°–43° C. In this way, after this instant, an atmosphere of 42°–43° C. and high humidity is maintained in the sauna booth. Since the steam sauna of the present invention is of the closed circulation type, the heat energy of the circulating fluid does not escape directly to the outside, thereby making efficient use of heat. Further, since the steam is produced by causing the fog generated by the ultrasonic unit to contact with the pre-heated room air, it is possible to create an atmosphere of comparatively low temperature and high humidity easily by the use of a heat source of small capacity.

According to the present invention, the steam for making the inner space much humid is obtained by the ultrasonic unit; hence, it is not necessary to heat to 100° C. and to boil the reserved water, in contrast to the conventional system. Therefore, a small capacity is enough for the heat source to heat the room air to a proper temperature; hence, the amount of heat energy used for operation can be reduced remarkably as compared with the prior art. The circulating fluid, which is a mixture of steam and hot air, repeatedly circulates through the closed passage, and the heat energy of the circulating fluid does not escape directly to the outside, in contrast to the prior art; hence, the heat efficiency is excellent. Because the closed circulation passage is provided, the atmospheric condition can be easily uniformed throughout the inner space. Since the wall surface of the sauna booth is previously heated by the hot air, the heat energy of the circulating fluid is not taken away by the wall surface; hence, no dew condensation appears on the wall surface. Further, the steam sauna of the present invention is usable as a hot air sauna by supplying hot air alone, and can further enhance the intrinsic effect of the sauna by repetitively operating it in a steam sauna mode and in a shower mode.

PREFERRED EMBODIMENTS

The construction of the present invention will now be described with reference to embodiments shown in the drawings.

Figure 1:
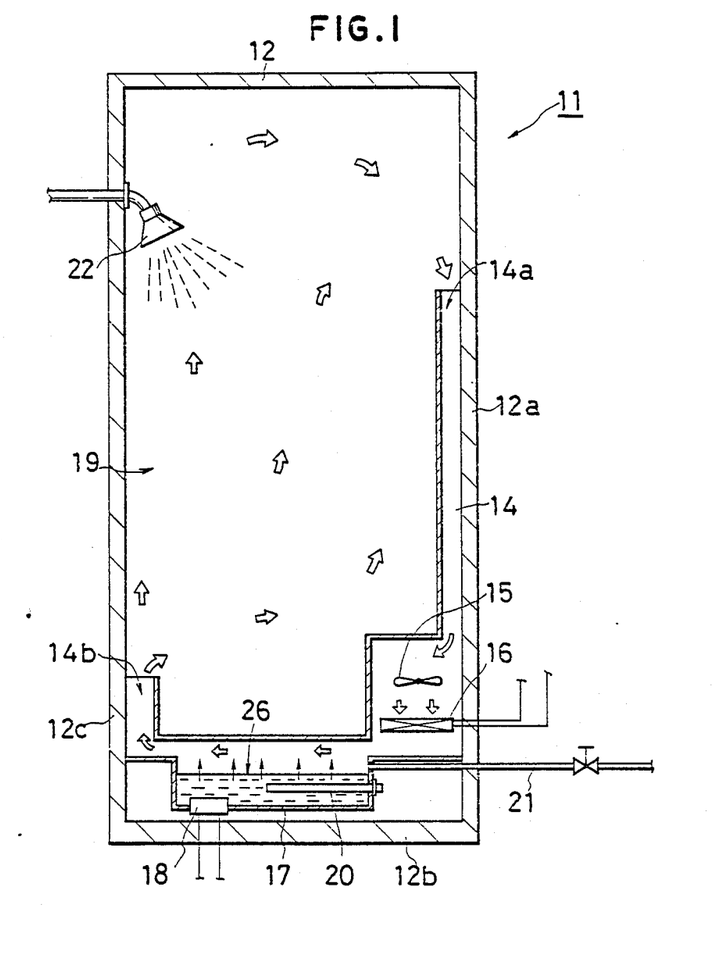
FIG. 1 is a vertical sectional view showing a sauna booth of a steam sauna according to a first embodiment of the present invention.

FIG. 1 is a vertical sectional view showing a sauna booth 12 of a steam sauna 11 according to a first embodiment of the present invention. In this embodiment, as shown in the drawing, a passage 14 is provided for circulating the inside air of a room along individual wall surfaces, which extends from a little above a central section of one side wall surface 12a of the sauna booth 12, along the whole area of a bottom wall surface 12b, to a little below a central section of another side wall surface 12c facing opposite the one side wall surface. An opening formed on the side of the side wall surface 12a serves as an inflow port 14a, and another opening formed on the side of the side wall surface 12c as an outflow port 14b. Thus, with these ports there is formed a closed circulation passage for the room air between the inside of the room 19 and the passage 14. In this embodiment, the passage 14 includes a fan 15 for forcibly sending air, a heater or heating means 16 for heating the room air, and a water tank 17. The water tank 17 is disposed so that its water surface 26 is exposed to the passage 14. The water tank includes an ultrasonic unit 18 for changing a reserved water stored in the tank into like a fog and supplying the foy to the passage 14, and a heater 20 for heating the reserved water. Reference numeral 21 designates a water supply pipe for supplying water to the water tank 17. A shower unit 22 is provided in an upper section of the side wall surface 12c of the sauna booth 12.

The operation of the steam sauna 11 of the foregoing configuration will now be described.

At the beginning, the fan 15, the heater 16 for heating the room air, and the heater 20 for heating the reserved water are put into operation. As a resul, the air in the room 19 is inhaled from the inflow port 14a into the passage 14, which passes through the fan 15 and the heater 16 and above the water tank 17, and reaches the outflow port 14b where it is discharged into the room 19, whereby a circulating air stream is formed. This circulating air stream is heated by the heater 16 to 40°–45° C., there by becoming hot air. In this way, the room air in the sauna booth 12 is previously heated. After a temperature equilibrium state or the most pleasant serviceable condition is reached in the whole room air, the ultrasonic unit 18 is put into operation. As a result, the reserved water in the water tank 17, which is previously heated by the heater 20 to a given temperature of 65°–75° C., repeats minute vibration, whereby a fog is generated from the reserved water surface 26 and supplied to the passage 14. The circulating air thus warmed comes into contact with the fog and instantly vaporizes it, so that a mixed circulating fluid of hot air and steam is generated. This circulating fluid is discharged from the outflow port 14b into the room 19; accordingly, an atmosphere of 42°–43° C. and high humidity is progressively created in the room 19.

According to the foregoing configuration, the heat energy of the circulating fluid of steam and hot air cannot be taken away because every wall surface of the sauna booth 12 is previously heated by the hot air, whereby no dew condensation appears on every wall surface. Since the circulating fluid repeatedly circulates through the closed passage, the heat energy of the circulating fluid cannot escape directly to the outside, so that the heat energy is efficiently utilized, whereby a hot and humid atmosphere of 42°–43° C. can be created in a short time. Because the circulation passage is provided, the atmosphere condition can be easily uniformed throughout the room 19. Heating to 100° C. and boiling the reserved water as in the prior art are not necessary in the present invention; thus, there is no need for a large-size heating means. Incidentally, the heater 20 provided in the water tank 17 is used to heat the reserved water to a given temperature to thereby promote generation of a fog; therefore, without this heater 20, it is also possible to generate a fog using the ultrasonic unit 18 alone. For reference, some parameters of this exemplary steam sauna 11 are: the volume of the sauna booth 12=1.2 m², and the heat capacity of the heater 16 serving as a room air heating means =800 W. From making a comparison in heat capacity between the heater 16 of the present invention and the conventional heater 16 ( of 3200 W or more ) shown in FIG. 3, it will be clear that the present invention utilizes a smaller heat capacity efficiently to create an atmosphere of low temperature and high humidity. According to our experiment performed to create an atmosphere of 42°–43° C. and 100% relative humidity in the same-volume sauna booth using the conventional system and the present invention system, the present invention system took 15 minutes as compared with 30 minutes of the conventional system.

The steam sauna 11 of the embodiment, of course, can be used as a hot air sauna by turning off the ultrasonic unit 18 and the heater 20 provided in the water tank and circulating mere hot air by means of the fan 15 and the heater 16. Further, as described hereinabove, where the steam sauna 11 includes the sauna boot 12 which is used in a closed state, the intrinsic effect of the sauna can be further enhanced if used in accordance with the steps of operating it in a steam sauna mode, terminating this mode, washing a sweating body with cold water or the like by the shower unit 22, operating again in the steam sauna mode, and repeating the above.

Figure 2:
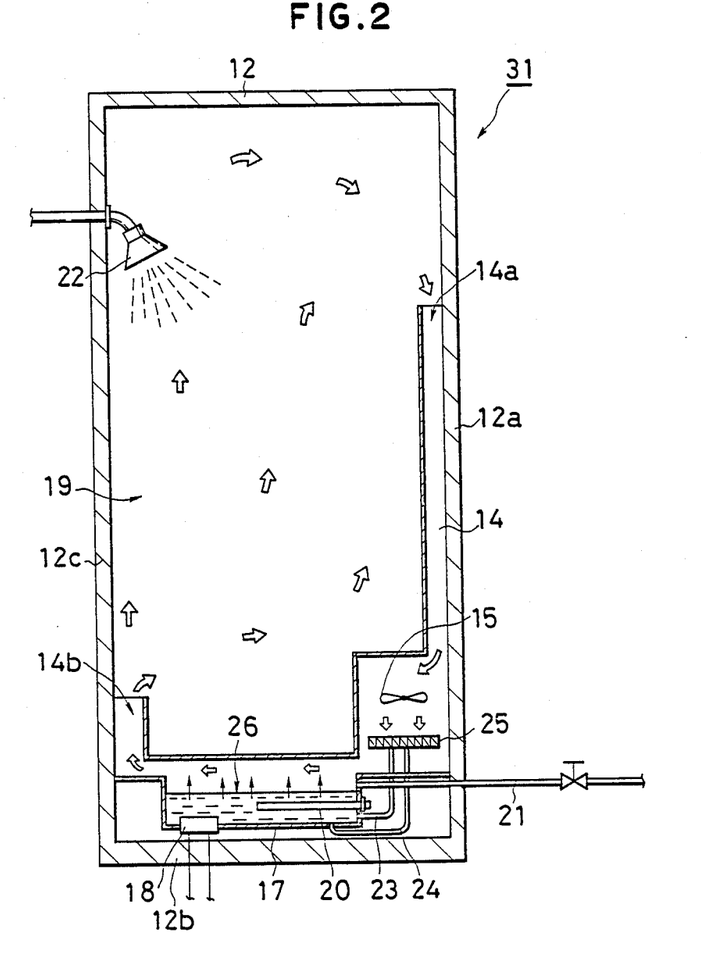
FIG. 2 is a vertical sectional view showing a sauna booth according to a second embodiment of the present invention.

FIG. 2 is a vertical sectional view showing a sauna booth 12 of a steam sauna 31 according to a second embodiment of the present invention. As shown in the drawing, instead of the heater 16 of the first embodiment, this embodiment includes a heat exchanger 25 disposed on the downstream side of the fan 15 which utilizes hot water stored in the water tank 17. Reference numerals 23 and 24 designate a supply pipe and a return pipe for the hot water, respectively, for connection between the water tank 17 and the heat exchanger 25. The heat exchanger 25 performs heat exchange between the hot water heated to a give temperature by the heater 20 provided in the water tank 17 and the room air passing through the passage 14, thereby heating the room air to a given temperature. The other components and effects of this second embodiment are identical with those of the first embodiment; hence, no further description is given here.

The present invention, of course, should not be limited to the aforementioned embodiments, but can be modified properly. For example, the inflow port 14a of the passage 14 may be formed at several positions inside the sauna booth 12, or may be made so elongate as to reach the other side wall surfaces. The heating means for heating the room air may be replaced with a plurality of ceramic heater elements, each including within its ceramic material an exothermic circuit having a temperature self-control function ( a PTC characteristic ), which are arranged side by side and stacked in layered form. Where the ceramic heater unit is employed, all the exothermic circuits are covered with the ceramic material, so that protection against moisture is excellent, the service life last long, and the electrical safety is secured. Further, the heating means may be a heat exchanger of the type whose heat source is gas or the like.

FIGS. 4 through 10 show a steam sauna 41 according to a third embodiment of the present invention. A bottom section of the steam sauna 41 comprises a base plate 42, and a waterproof pan 44 is disposed above the base plate with a space 43 left between them. This waterproof pan 44 is made of FRP ( glassfibre reinforced plastics ), and is integrally molded with a column section 45 shown in FIG. 6 and 7, a side skirt section 46 shown in FIG. 5, a booth floor section 47, a seat section 48, a panel mounting section 49, and the like. The waterproof pan 44 has a drain trap 50. On the side panel mounting section 49 are erected an inner panel 52, frames 53, and outer panels 54.

Figure 5:
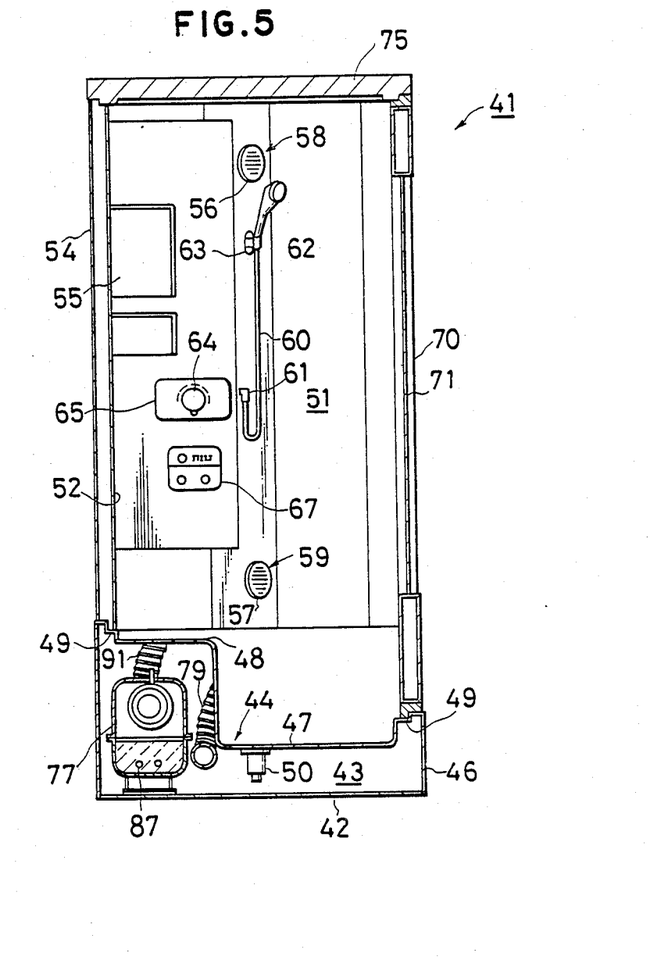
FIG. 5 is a sectional view taken along line A—A' in FIG. 4.

As shown clearly in FIG. 5, the inner panel 52 is provided with a shelf 55 having a U-shaped recess and projecting from a booth room 51 toward the outside thereof, which shelf is adapted to receive a shampoo, rinse, shaver, etc. The inner panel 52 made of FRP is formed with openings for incoming and outgoing of gas with respect to the booth room, to which openings air hole members 56 and 57 with slits are attached to define an inlet port 58 and an outlet port 59. The inner panel 52 has a connection fixture 61 for the base end of a shower hose 60, a hook 63 for a shower head 62, a thermostat mixing valve 65 with a handle 64 for regulation of the flow rate and temperature of a shower, and an inside control board 67 with switches for control of the temperature and humidity of air discharged into the booth room 51 and for control of a ventilating fan 66 shown in FIG. 6. The inner panel 52 also supports a panel-type far infrared radiation heater 68 for irradiating a body staying in the booth 51 with far infrared rays.

Figure 6:
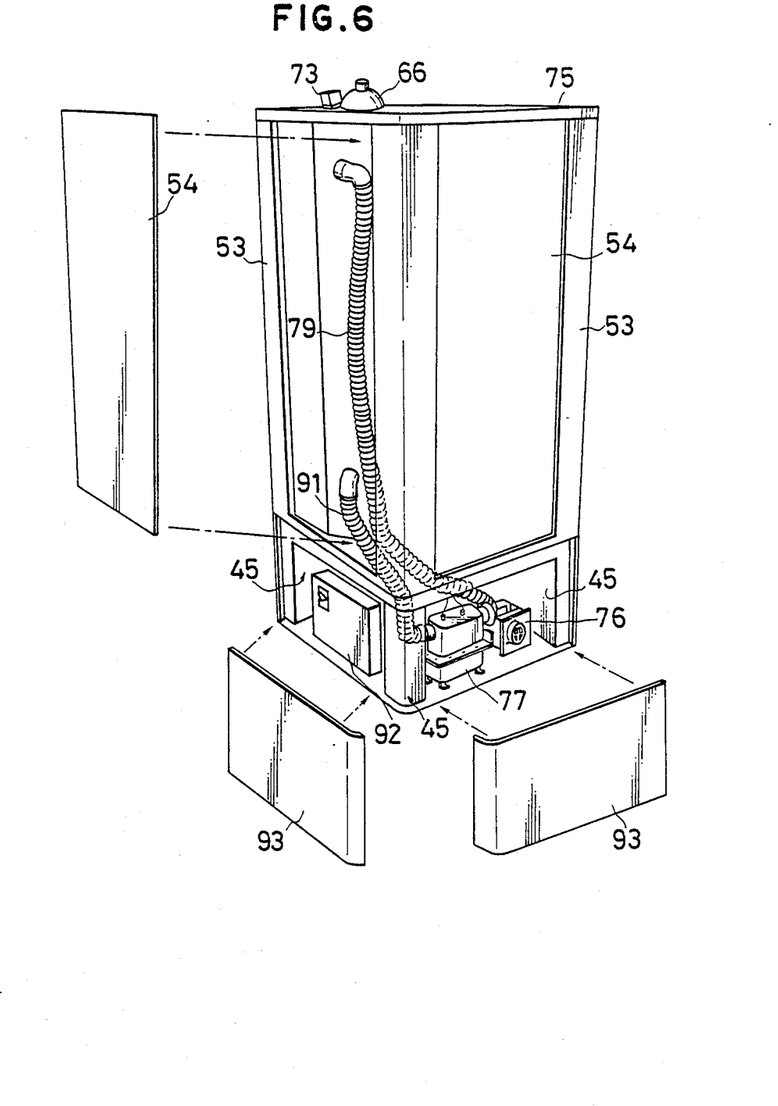
FIG. 6 is a perspective view, partly exploded, of a steam sauna.
Figure 10:
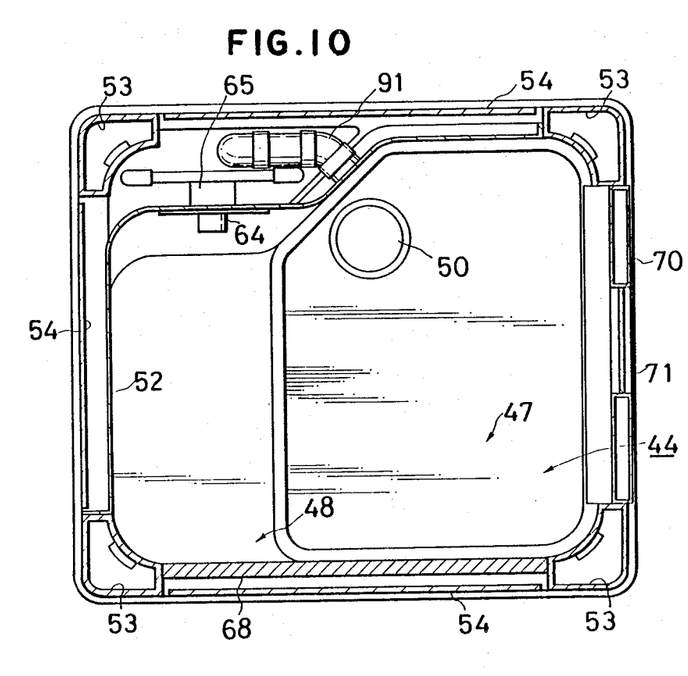
FIG. 10 is a sectional view taken along line C—C' in FIG. 4.

As shown in FIG. 6 and 10, the frames 53 made of FRP stand upright at the four corners of the waterproof pan, to which the three outer panels 54 are detachably attached to facilitate inspection of internal piping, electric wiring, and the like. One side of these frames where no outer panel is attached is provided with a door 70. This door has a translucent glass 71 attached thereto. An outside control board 72 is provided adjacent to the door 70. This control board includes a main switch for electric units of the sauna booth and a switch for a ceiling lamp 73. A ceiling panel 75 is mounted on the upper ends of the frames 53, to which the lamp 73 for illuminating the booth room and the fan 66 for ventilating the booth room are attached.

Figure 7:
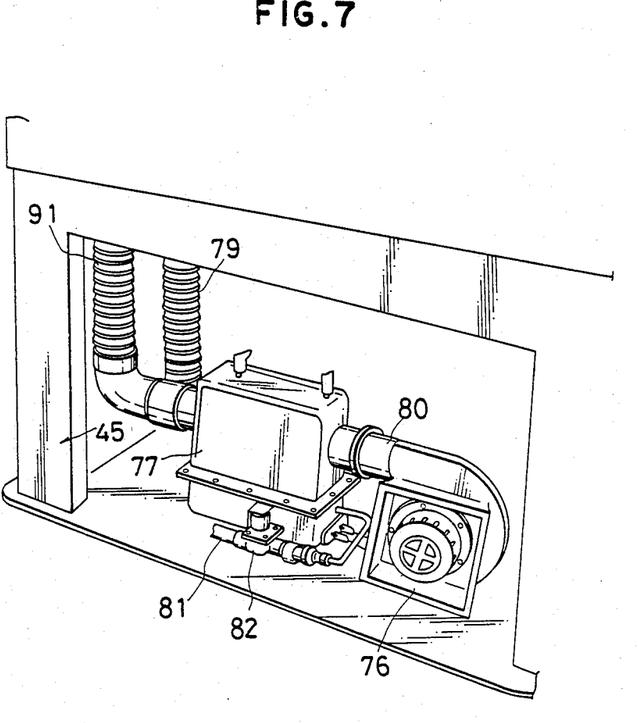
FIG. 7 is a perspective view of a bottom section of the steam sauna.

As shown in FIG. 7 in enlarged view, on the under side of the seat section 48 of the waterproof pan 44 are provided a blower 76 and a steam generator 77. The inlet port of the blower 76 is connected through a flexible duct 79 to the inlet port 58 of the inner panel 52 and its outlet port 80 to the steam generator 77.

Figure 8:
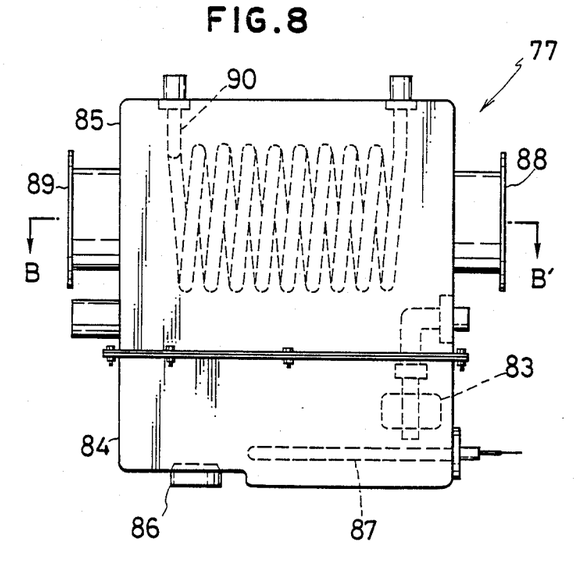
FIG. 8 is a side view of a steam generator.
Figure 9:
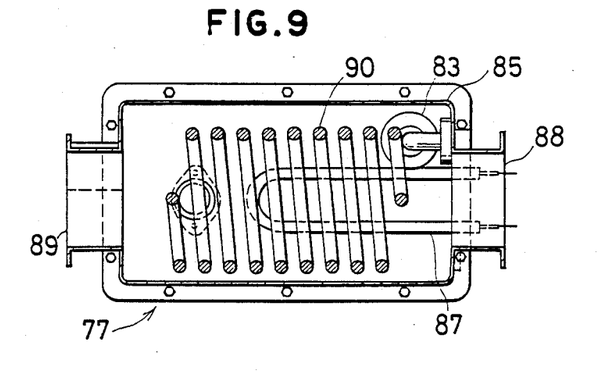
FIG. 9 is a plan view of the steam generator.

The steam generator 77 is connected via an electromagnetic valve 82 to a water supply pipe 81, and the open/close control of the electromagnetic valve 82 is effected in response to a signal from a float switch 83 provided inside the steam generator 77 so as to give a certain water level always. The steam generator 77 is provided with a water tank formed by a pan 84 and a cover 85, to this pan 84 being attached an ultrasonic generator 86 and a heater 87 for heating water electrically. The cover 85 is formed with a gas inlet port 88 and a gas outlet port 89 and provided with a heater 90 for electrically heating an air stream passing from the inlet port 88 to the outlet port 89. The outlet port 89 is connected through a flexible duct 91 to the outlet port 59 of the inner panel 52.

As shown in FIG. 6, on the under side of the waterproof pan 44 is provided an electric circuit box 92 in which circuits are accommodated for controlling electric units of the steam sauna, such as the blower 76, ultrasonic oscillator 86, and heaters 87 and 90, in response to signals from the control boards 67 and 72. To each side of the waterproof pan 44 is detachably attached a panel 93.

In the sauna shown in FIGS. 4 through 10, the outside dimensions of the booth are 90×100 cm in horizontal plane and 215 cm in hight. The maximum airflow rate of the blower 76 is on the order of 2 m$^3$/Hr.

The water heating heater 87 of the steam generator 77 is rated to 600 W, and the air heating heater 90 to 1000 W. In the normal operating state where the steam generator 77 and the blower 76 are in operation, the booth room 51 can be maintained at a relative humidity of 98% or more and a temperature of 42° C. When the outside air temperature is 15° C., the electric power consumed in the steam sauna, exclusive of those for the lamp 66 and the ventilating fan 73, is about 1600 W, this corresponding to about 50% of the electric power consumed in the conventional steam sauna shown in FIG. 3 of substantially equivalent dimensions.

In the thus configured steam sauna, a user goes in and out while opening the door 70. According to a normal operating procedure, prior to entering the booth room 51, the blower 76, heaters 87 and 90, and ultrasonic oscillator 86 are put into operation. After the booth room 51 becomes hot and humid enough, the user enters the booth room in which he or she warms up one's body and/or takes a shower. The airflow rate discharged from the outlet port 58 can be regulated by operating the switch on the inside control board 67 to control the rotating speed of the blower 76. The airflow temperature discharged can be regulated by switching operation of the control board to control the output of the air heating heater 90. The airflow humidity can be regulated by controlling the output of the ultrasonic oscillator 86. Similarly, the output of the far infrared radiation heater 68 can be regulated, and the ventilating fan 73 can be turned on and off. Of course, the "output regulation" control also means to turn off an object unit. Using the thus configured steam sauna, it is possible to control the booth room temperature and humidity and the far infrared radiation heater 68 and to create an atmosphere best suited for the booth user while staying in the booth room 51.

Incidentally, without the far infrared radiation heater 68 the user can enjoy the steam sauna well comfortably.

Figure 11:
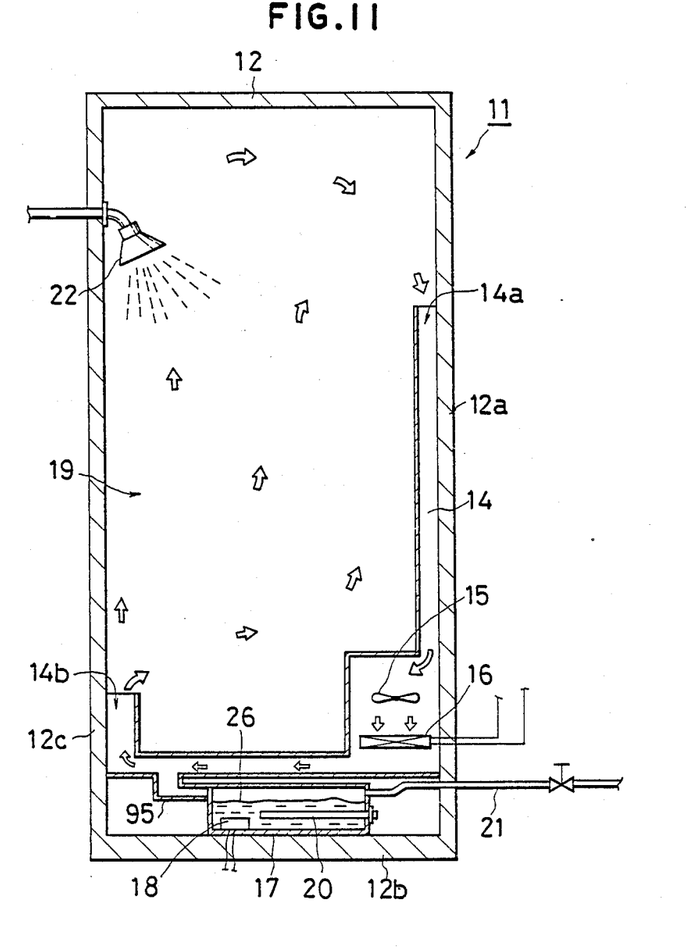
FIG. 11 is a vertical sectional view of a sauna booth according to a fourth embodiment of the present invention.

Although in the foregoing embodiment the circulating airflow is in direct contact with the surface of the reserved water in the water tank 17, the present invention can also be implemented in such a manner that as shown in FIG. 11, the water tank 17 is made independent of the passage 14 for the circulating airflow, and the steam generated at the water tank 17 is introduced through, for example, a duct 95 into the passage 14. In this modified configuration, a damper (not shown) may be provided midway along the duct 95 to regulate the amount of steam to be supplied to the passage 14.

Figure 12:
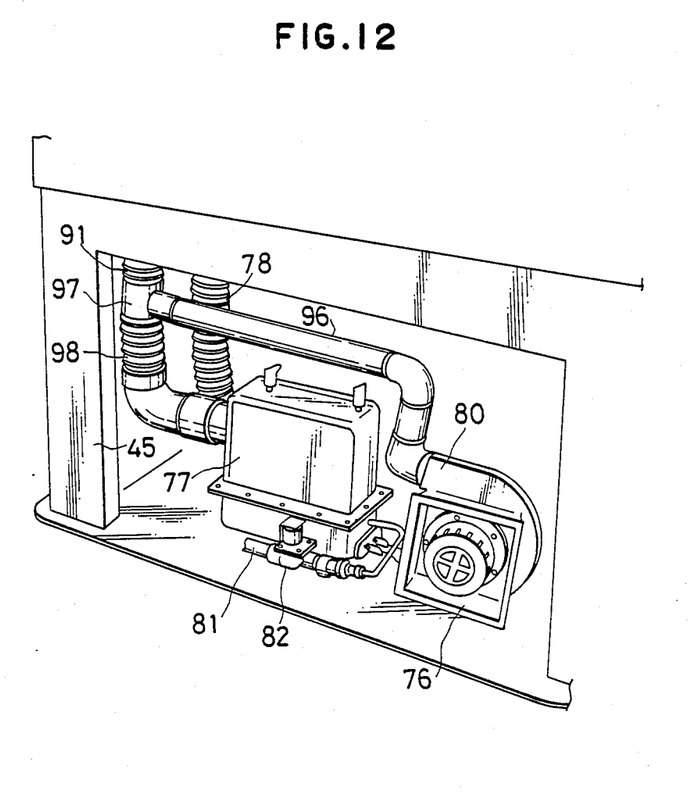
FIG. 12 is a perspective view showing in greater detail, a bottom section of the sauna booth of FIG. 11.

FIG. 12 is a perspective view showing the surrounding arrangement of the steam generator 77 that will be embodied if the feature of FIG. 11 is applied to the steam sauna 41 shown in FIG. 4 through 10. In FIG. 12, the airflow sent out of the blower 76 is supplied through a pipe 96 including an air heater and a T-type joint 97 to the flexible duct 91. The steam generated in the steam generator 77 is supplied through a short flexible duct 98 and the T-type joint to the flexible duct 91. The other components not mentioned above of FIG. 12 are identical with those of FIG. 7.

Figure 13:
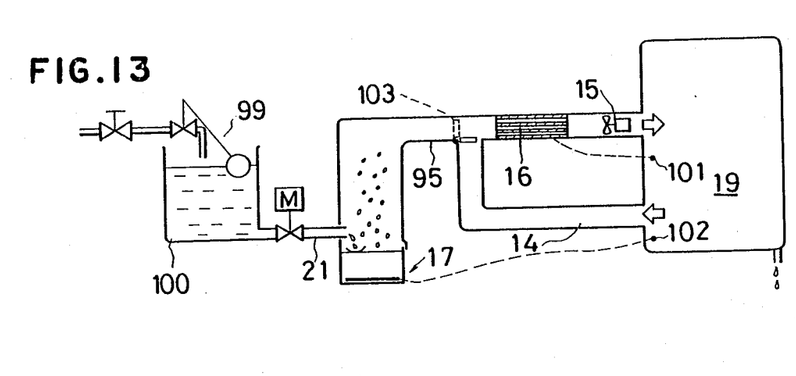
FIGS. 13, 14 and 15 are schematic sectional views showing sauna booths according to other embodiments of the present invention.
Figure 14:
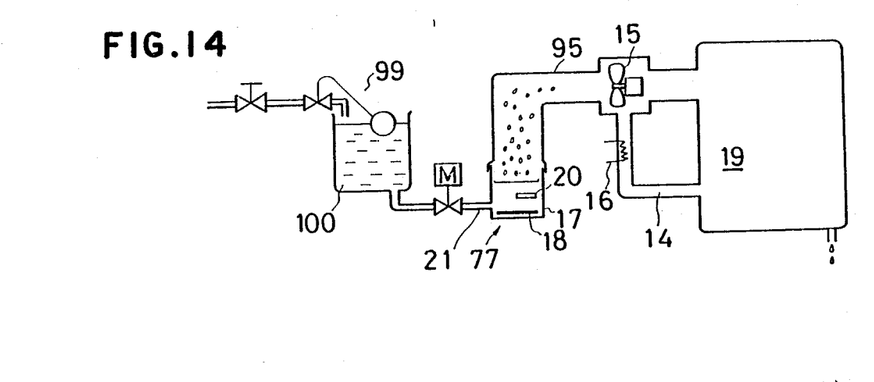
Figure 15:
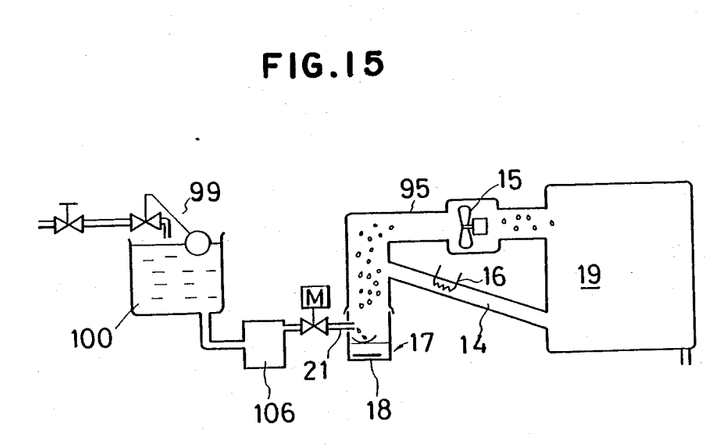

FIGS. 13 through 15 show other embodiments of the present invention. In FIG. 13, steam is supplied from the water tank 17 containing the ultrasonic oscillator 18 through the duct 95 to the passage. Water is supplied from a water tank 100 through the pipe 21 to the water tank 17. Of course, water is supplied through a float valve 99 to the water tank 100 also so that the water level of this tank can always be maintained constant. The passage 14 has the fan 15 and the air heater 16 provided thereinside. The air heater 16 is preferably a PTC heater having a PTC (positive resistance-temperature characteristic) property. In FIG. 13, there are provided a temperature sensor 101 for detecting the temperature of the room 19 and a humidity sensor 102 for detecting the humidity thereof, in response to their detection signal the heater 16 and the ultrasonic oscillator 18 being controlled so that the temperature and humidity of the room 19 can take respective desired values. The junction section of the duct 95 and the passage 14 includes a damper 103 so that both the flow rate of circulating airflow and the amount of steam being added can be regulated.

The configuration of FIG. 14 differs from that of FIG. 13 in that the damper 103 and the sensors 101 and 102 are omitted, but the fan 15 is provided in the junction section of the passage 14 and the duct 95. In the water tank 17 are provided the ultrasonic oscillator 18 and the water heater 20.

The configuration of FIG. 15 differs from that of FIG. 14 in that a water heater 106 is provided in the pipe 21 between the water tank 100 and the ultrasonic oscillator 18 so that water can be heated to about 50°–60° C. Incidentally, the fan 15 is provided somewhere on the downstream side of the junction section of the duct 95 and the passage 14.

We claim:

1. A steam sauna comprising:
   a sauna booth having an upper portion and a lower portion,
   a passage extending from the upper portion to the lower portion inside the sauna booth, air in the sauna booth being able to circulate through the passage,
   air sending means provided in said passage for circulating the air,
   heating means provided in said passage for heating the circulating air, and
   steam generating means with an ultrasonic oscillator for generating steam which is disposed so that the generated steam can be mixed with the air flowing through said passage.

2. A steam sauna according to claim 1, wherein said sauna booth is provided with a shower unit.

3. A steam sauna according to claim 2, wherein said sauna booth is provided with a floor made of a waterproof pan with a drain trap.

4. A steam sauna according to claim 3, wherein said waterproof pan has a seat section on which a user can sit down, and on the under side of said seat section are provided said steam generating means and said air sending means.

5. A steam sauna according to claim 1, wherein the air flowing through said passage is made to pass through said steam generating means.

6. A steam sauna according to claim 5, wherein said air heating means is provided in said steam generating means.

7. A steam sauna according to claim 1, wherein the steam generated in said steam generating means is led through a steam guiding member to said passage.

8. A steam sauna according to claim 1, wherein said steam generating means includes a heater for heating water to be vaporized.

* * * * *